United States Patent
Coelho et al.

[11] Patent Number: 6,146,124
[45] Date of Patent: Nov. 14, 2000

[54] FREEZING AND THAWING BAG, MOLD, APPARATUS AND METHOD

[75] Inventors: Philip Henry Coelho, El Dorado Hills, Calif.; Pablo Rubinstein, New Rochelle, N.Y.

[73] Assignee: ThermoGenesis Corp., Rancho Cordova, Calif.

[21] Appl. No.: 08/670,368

[22] Filed: Jun. 25, 1996

[51] Int. Cl.[7] .................................................. B29C 51/30
[52] U.S. Cl. ........................ 425/387.1; 425/388; 425/403
[58] Field of Search .................................... 425/383, 385, 425/387.1, 388, 394, 395, 398, 403

[56] References Cited

U.S. PATENT DOCUMENTS

| | | |
|---|---|---|
| 3,545,671 | 12/1970 | Ross . |
| 3,576,650 | 4/1971 | Underwood et al. . |
| 3,616,033 | 10/1971 | Rausing . |
| 3,654,012 | 4/1972 | Schlager . |
| 3,755,040 | 8/1973 | Robinson . |
| 3,801,402 | 4/1974 | Suter . |
| 3,861,977 | 1/1975 | Wiley . |
| 3,968,829 | 7/1976 | Naakta et al. . |
| 3,999,930 | 12/1976 | Telbizoff . |
| 4,076,063 | 2/1978 | Cammarata, III et al. . |
| 4,105,730 | 8/1978 | Cammarata, III et al. . |
| 4,131,200 | 12/1978 | Rinfret . |
| 4,152,184 | 5/1979 | Bacehowski . |
| 4,162,884 | 7/1979 | Vetter ........................................ 425/388 |
| 4,191,231 | 3/1980 | Winchell et al. . |
| 4,397,804 | 8/1983 | Medwed .................. 425/388 |
| 4,425,177 | 1/1984 | Shinno . |
| 4,428,743 | 1/1984 | Heck . |
| 4,453,940 | 6/1984 | Aoyagi et al. . |
| 4,460,365 | 7/1984 | Gánshirt et al. . |
| 4,467,588 | 8/1984 | Corveth ..................... 53/425 |
| 4,469,227 | 9/1984 | Faust . |
| 4,484,920 | 11/1984 | Kaufman et al. . |
| 4,588,401 | 5/1986 | Kilkson . |
| 4,591,357 | 5/1986 | Sneider . |
| 4,613,640 | 9/1986 | Deisler et al. . |
| 4,645,482 | 2/1987 | Yoshida . |
| 4,657,542 | 4/1987 | Ohachi . |
| 4,717,377 | 1/1988 | Fukasawa . |
| 4,854,737 | 8/1989 | Steer et al. . |
| 4,943,222 | 7/1990 | Nathoo ...................................... 425/89 |
| 5,018,622 | 5/1991 | Hartley . |
| 5,023,119 | 6/1991 | Yamakoshi . |
| 5,066,290 | 11/1991 | Measells et al. . |
| 5,108,387 | 4/1992 | Falk et al. . |
| 5,108,532 | 4/1992 | Thein et al. . |
| 5,126,175 | 6/1992 | Yamakoshi . |
| 5,176,258 | 1/1993 | Antal . |
| 5,198,175 | 3/1993 | Kato et al. ............................... 264/512 |
| 5,226,564 | 7/1993 | Steer et al. . |
| 5,300,059 | 4/1994 | Rubinstein et al. . |
| 5,364,385 | 11/1994 | Harms et al. . |
| 5,375,701 | 12/1994 | Hustad et al. . |
| 5,379,895 | 1/1995 | Foslien . |
| 5,394,907 | 3/1995 | Hjertman et al. . |
| 5,431,496 | 7/1995 | Balteau et al. . |
| 5,439,100 | 8/1995 | Gordon et al. . |
| 5,474,169 | 12/1995 | Bauman . |
| 5,477,660 | 12/1995 | Smith ....................................... 53/433 |
| 5,485,919 | 1/1996 | Samberg et al. . |
| 5,486,390 | 1/1996 | Burns et al. . |
| 5,509,898 | 4/1996 | Isono et al. . |
| 5,545,370 | 8/1996 | Moren et al. ............................ 264/522 |
| 5,637,330 | 6/1997 | Younessian et al. .................... 425/183 |
| 5,638,686 | 6/1997 | Coelho et al. . |
| 5,772,880 | 6/1998 | Lynn et al. . |

FOREIGN PATENT DOCUMENTS

| | | |
|---|---|---|
| 455916 | 4/1949 | Canada . |
| 23 43 453 | 7/1975 | Germany . |
| 3-197031 | 8/1991 | Japan . |
| 627990 | 10/1978 | Russian Federation . |

*Primary Examiner*—James P. Mackey
*Attorney, Agent, or Firm*—Bernhard Kreten

[57] ABSTRACT

A mold is disclosed for forming a freezable and thawable bag of uniform thickness, especially useful for cryopreservation of thermolabile substances. The mold features one or more recessed planar surfaces, including radiused peripheral walls about the recesses, a planar top surface, and means for conforming a blank sheet to the mold. Two mold halves combine to form a completed bag. The mold halves may be complimentary.

56 Claims, 6 Drawing Sheets

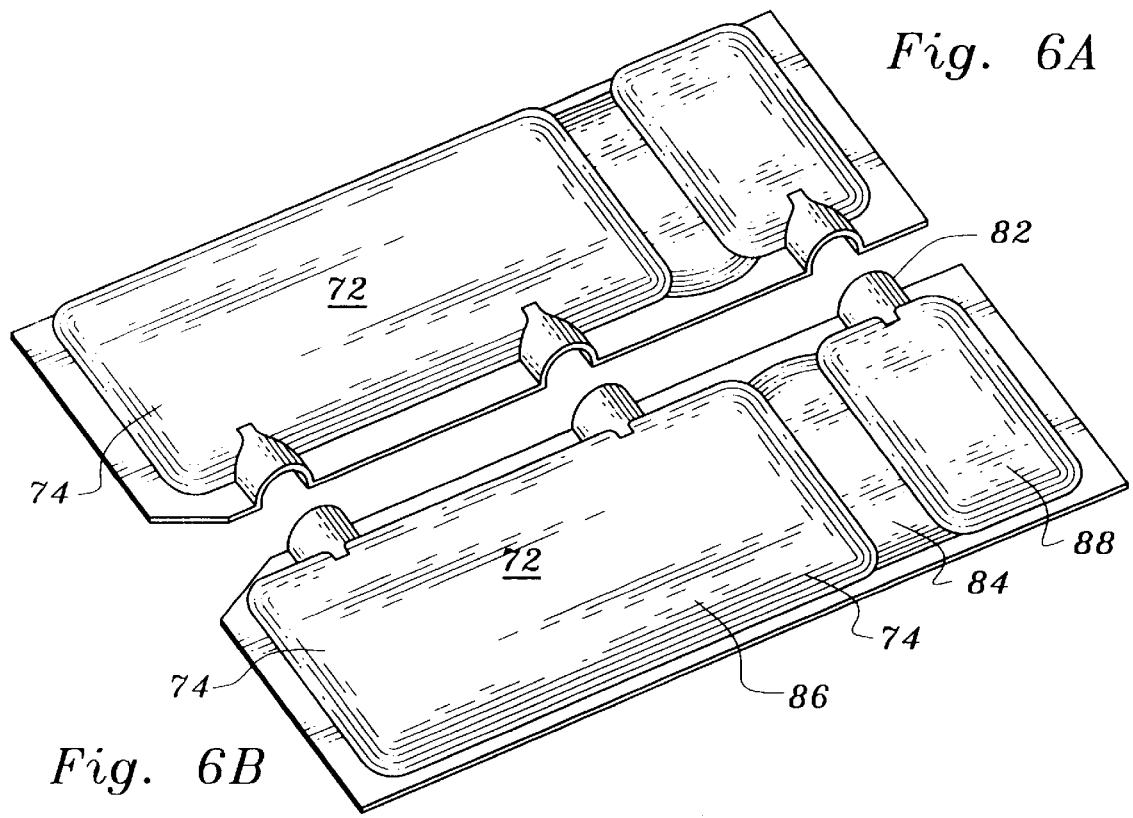
Fig. 6A
Fig. 6B
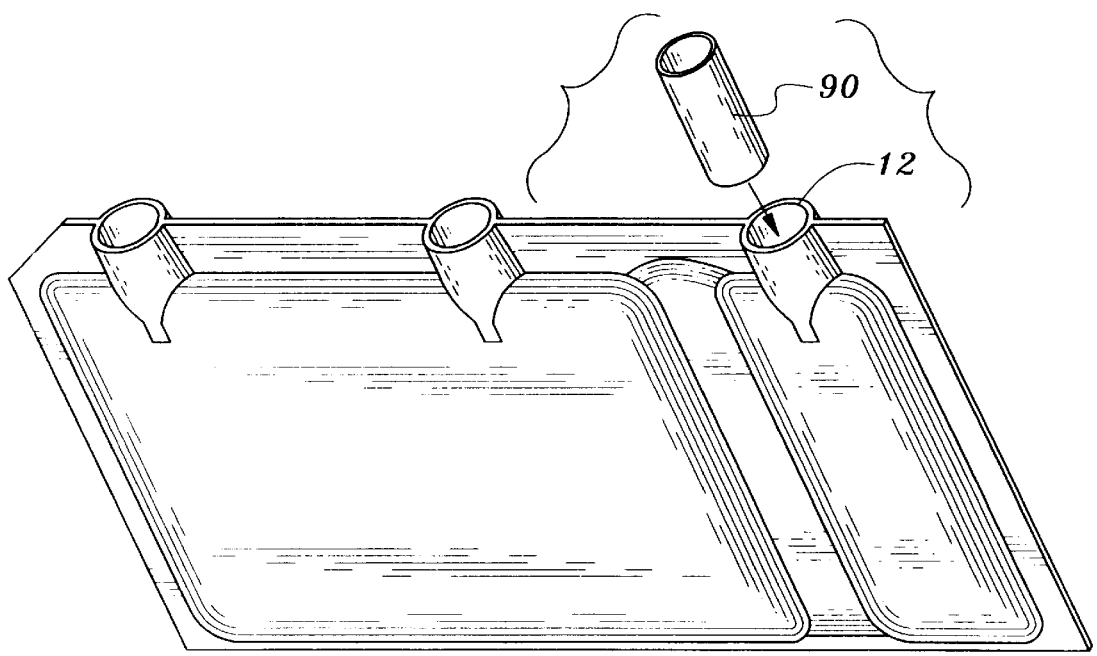
Fig. 6C

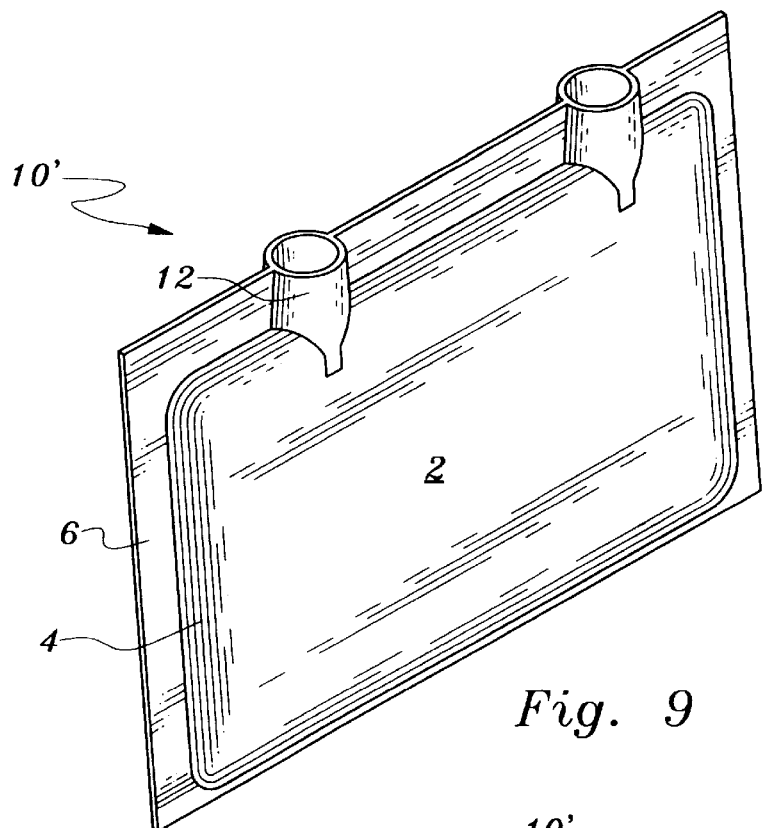
*Fig. 9*
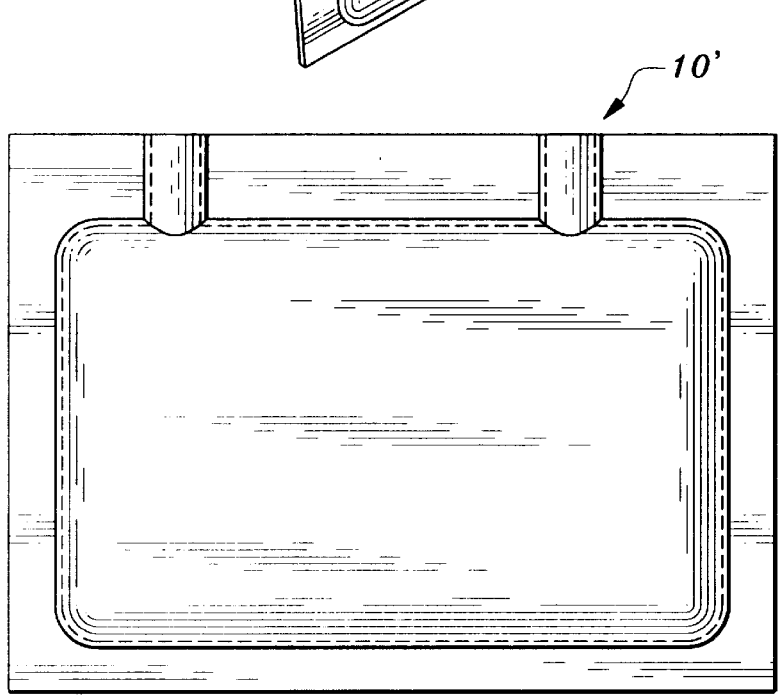 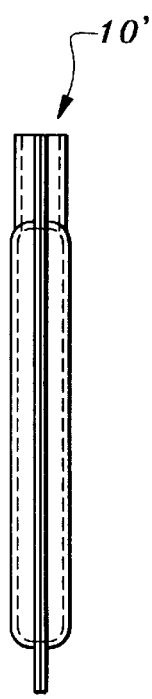
*Fig. 10* *Fig. 12*
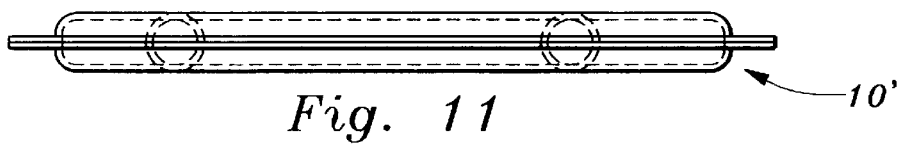
*Fig. 11*

FREEZING AND THAWING BAG, MOLD, APPARATUS AND METHOD

FIELD OF THE INVENTION

The following invention relates to an apparatus for forming flexible bags, a method for forming the flexible bag and the bag itself. More specifically, the following invention relates to bags to contain thermolabile and/or cellular biological substances and formed such that they can withstand stresses at extremely cold, cryogenic temperatures, reduce heat invasion from a higher ambient temperature into a plurality of such bags placed together, reduce storage space required for a plurality of such bags, and provide a thin and substantially constant cross-section for the bag so that the rate of heat transfer into and out of the bag is substantially homogenous throughout the contents of the bag thereby providing an improved means of protecting the viability of living cells during freezing and thawing.

BACKGROUND OF THE INVENTION

Preservation of blood, cellular biological substances, tissue and other thermolabile products frequently involves product maintenance at extremely cold temperatures. Cellular biological substances are the fundamental, structural and functional unit of living organisms. Thermolabile substances are those substances which are easily altered or decomposed by heat. One economical mode for containment involves the use of encapsulating plastic since plastic is relatively inexpensive and lends itself to mass production techniques. However, many plastics suffer from brittleness at extremely low cryogenic temperatures and seams are sometimes susceptible to fracture.

In addition, bags that are formed either by folding over a planar material and seaming along peripheries or layering two planar materials and seaming along the peripheries have a generally ovoid shape when filled with a liquid. This is because the cross-sectional area adjacent either the fold or the seam has an area of decreasing cross-sectional width as it tapers from the center. While for many applications, this type of narrowing is unobjectionable, for certain biological fluids such as white stem cells, a bag having non-uniform thickness along its cross-section may impair the integrity of the biological product, particularly during temperature changes. One reason for quality loss during a change in temperature may involve the differential thermal gradient within the thermolabile or cellular substance caused by variations in thickness induced by the geometric shape of the bag itself. Stated alternatively, the center portion of the bag is thicker than the edges.

A corollary to the above-enunciated problem entails the fact that the prior art bags, with their thicker center portions, also provides a non-planar surface on opposing sides of the bag. This results in a "high spot" which also makes uniform temperature alteration of the contents difficult especially when heat exchange is attempted by contact with a substantially planar surface that provides the heat gradient. Because the bag has a high area, uniform contact along the entire cross-section of the surface will have been precluded.

FIG. 8 reflects prior art bag structure and highlights the inherent problems associated therewith. The radio frequency seam S is thinner than the non-seamed plastic forming the bag and has its weakest point W at an edge of the seal closest to the interior I. When the product P begins to freeze, the product freezes first at the thinnest part of the bag, i.e. at edge E. Freezing proceeds inwardly, from the outside in, until an unfrozen core C exists. As the core C freezes, it expands and generates forces F which collimate and focus on the edge E because of the geometrical configuration of the bag. The force F frequently causes bag rupture at the weakest point W because the wedging force appearing at edge E tries to separate the seam with a turning moment M. Recall the bag material tends to become brittle at low temperatures, exacerbating this problem.

FIG. 13 reveals a further site of prior art bag weakness. When an access port tube T is to be fitted to the bag, two horseshoe-shaped RF horns H close on the plastic membrane around the tube T and then the membrane at the seal area S. This causes another weakened area W where bag failures commonly occur.

SUMMARY OF THE INVENTION

The instant invention addresses all of the difficulties noted hereinabove. One manifestation of the problems solved includes the formation of peripheral seams circumscribing the bag which are appreciably stronger than prior art seam structures. Preferably, the bag is formed from two symmetrical sections, each vacuum formed to provide a major wall flanked by a radiused end wall section and circumscribed by a peripheral flange. It is contemplated in one form of the invention that two half portions defining a plane of symmetry are thus formed and adhered together so that the peripheral flanges are in mating registry and sealed such as by means of adhesive, ultrasonic, R.F. welding or other means. The increased surface area of the peripheral seam flange coupled with the radiused end wall interposed between the seam flange and the major wall of the bag dissipate forces which in prior art bags could have lent themselves to rupture at the seam area.

By vacuum forming the two halves, the contour of the side wall can be carefully controlled to make them substantially planar. Thus, when the two halves are united, a container having substantially uniform cross-section substantially along the entire extent will have been provided. This geometry encourages uniform thawing, freezing and imperviousness to the stresses that attend the seams and the radiused end wall at cryogenic temperatures. This geometry also provides space efficient storage and reduced heat invasion from a warmer ambient medium when the plurality of bags are placed with their planar surfaces in contact with each other.

OBJECTS OF THE INVENTION

Accordingly, it is an object of the present invention to provide a useful and novel bag for containing thermolabile or live cell products, a method for making same and an apparatus associated with the formation of the bag.

A further object of the present invention is to provide a device as characterized above in which the seams associated therewith have greater strength to improve the integrity of the bag.

A further object of the present invention is to provide a device as characterized above in which the major surfaces of the bag are closely spaced, parallel and substantially planar thereby increasing the likelihood that heat transfer along those planar surfaces will more uniformly alter the temperature profile of the contents within the bag.

A further object of the present invention is to provide a device as characterized above which lends itself to mass production techniques, is extremely safe to use and is durable in construction.

A further object of the present invention is to provide a device as characterized above which is substantially rectangular so as to allow the device to be stacked side by side and end to end with minimal wasted space thereby achieving space efficient storage at low temperatures which results in a reduced operating cost.

A further object of the present invention is to provide a device as characterized above which has two parallel planar surfaces which make up a high percentage of the total exterior surface of the container such that when two or more such containers, lowered to subzero temperatures, are placed in contact with each other along these large planar surfaces, the percentage of the total surface area of the combined containers available to absorb heat from a surrounding warmer medium is substantially reduced.

Viewed from a first vantage point, it is an object of the present invention to provide a bag comprising, in combination: a first bag portion having a substantially planar outer wall, a radiused edge wall circumscribing the planar outer wall and peripheral flashing circumscribing the radiused edge wall, a second bag portion sealed to the peripheral flashing and overlying the planar outer wall of the first bag portion such that the planar outer wall is spaced from the second bag portion by a dimension at least equal to a radius of the radiused edge wall.

Viewed from a second vantage point, it is an object of the present invention to provide a method for forming a bag, the steps including: forming a first mold having a recess including a planar surface, a radiused periphery circumscribing the planar surface and a peripheral ledge circumscribing the radiused periphery and oriented parallel to the planar surface, placing a blank of sheet material over the first mold, and causing the blank to conform to the mold, removing the formed sheet and enclosing the bag.

Viewed from a third vantage point, it is an object of the present invention to provide a bag formed by: deforming a first sheet of material to have a planar outer wall, a radiused edge wall circumscribing the outer wall and peripheral flashing circumscribing the edge wall oriented parallel to the outer wall and defining a pocket, sealing the pocket with a second sheet of material.

Viewed from a fourth vantage point, it is an object of the present invention to provide a mold for forming bags comprising, in combination: a recess including a planar surface, a radiused periphery circumscribing the planar surface and a peripheral ledge circumscribing the radiused periphery and oriented parallel to the planar surface, means for receiving a blank of sheet material over the recess and lapped atop the peripheral ledge, and means for conforming the sheet material blank to a contour of the mold.

These and other objects will be made manifest when considering the following detailed specification when taken in conjunction with the appended drawing figures.

BRIEF DESCRIPTION OF THE DRAWINGS

FIGS. 6(A–C) are perspective views of a first bag portion (6A), a second bag portion (6B) and the two portions placed in mating registry (6C).

FIG. 9 is a perspective view of an alternative to FIGS. 2 through 5.

FIG. 10 is a front view of FIG. 9.

FIG. 11 is a top view of FIG. 10.

FIG. 12 is an end view of FIG. 10.

DESCRIPTION OF PREFERRED EMBODIMENTS

Figure 1:
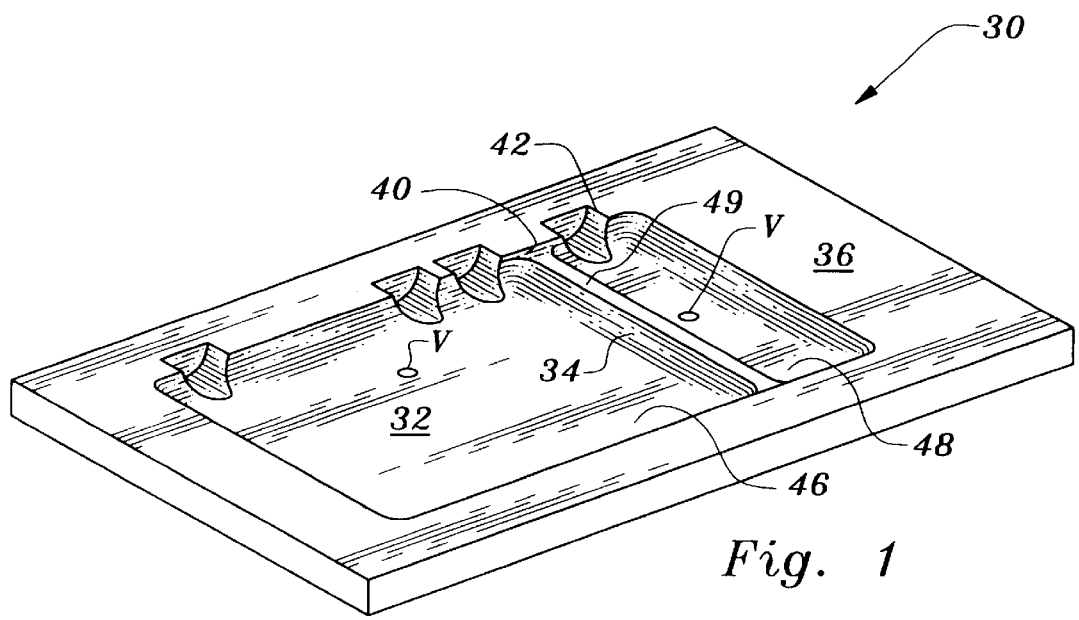
FIG. 1 is a perspective view of a female mold according to the present invention.

Referring to the drawings, wherein like reference numerals denote like parts throughout the various drawing figures, reference numeral 10 is directed to the bag according to the present invention.

In its essence, the bag is formed from a first half and a second half. Preferably each half includes a planar outer wall and a peripherally disposed radiused edge wall that terminates in peripheral flashing, the flashing oriented parallel to and spaced from the planar outer wall by the dimension of the radius. In a preferred form, each half forming the bag is a symmetrical mirror image of the other so that the overall thickness of the bag is twice the radius of either half. In another form of the invention, however, the bag can be formed as having a first half as above-described and a second half as a planar back wall overlying a recess formed by the first half and adhered to the first half by the peripheral flashing.

Figure 2:
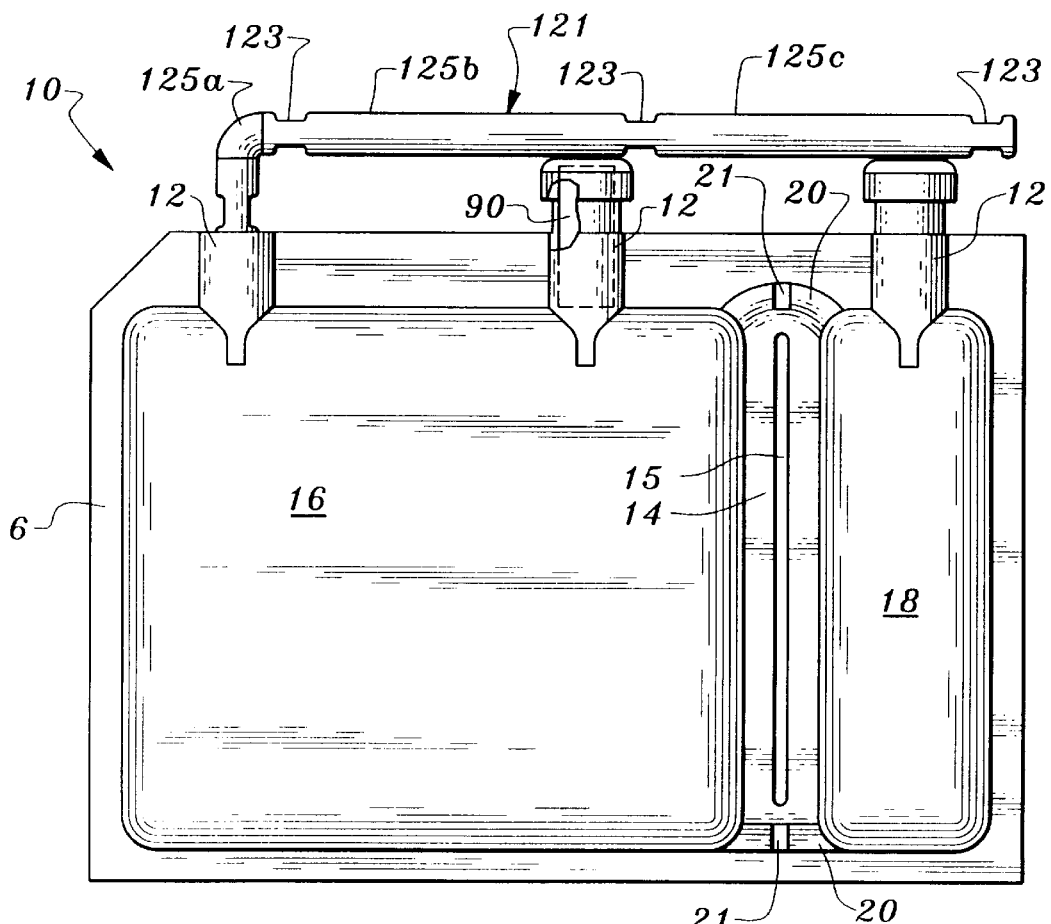
FIG. 2 is a side view of one type of bag that can be formed from the mold of FIG. 1.
Figure 3:
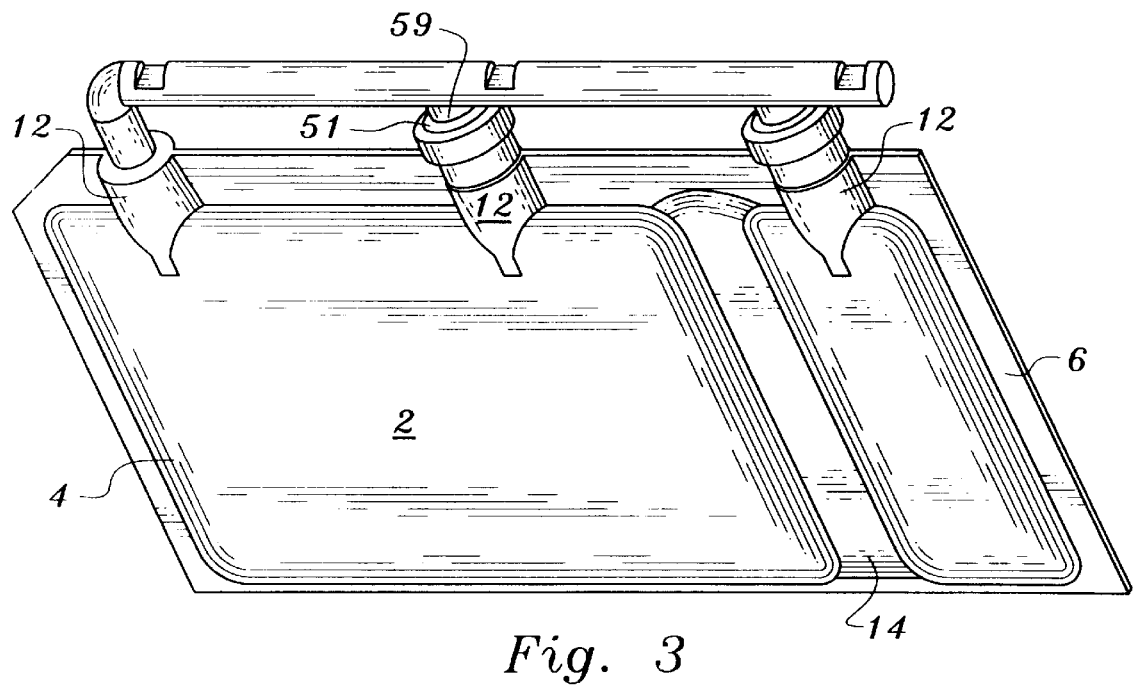
FIG. 3 is a perspective view of FIG. 2.
Figures 4, 5:
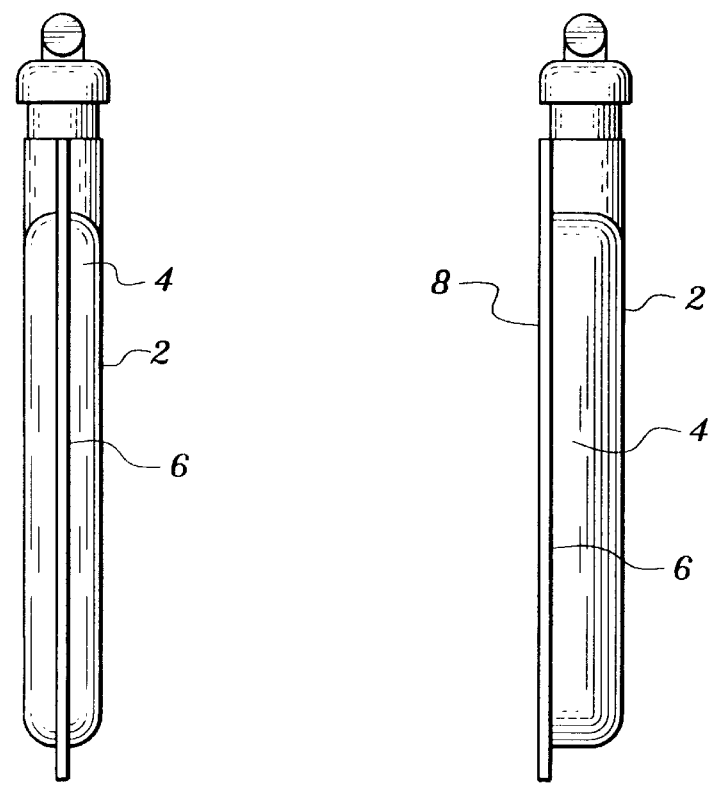
FIG. 4 is an end view of FIG. 2.
FIG. 5 is an alternate to FIG. 4.

More particularly, the bag as shown in FIGS. 2 through 4 include a planar outer wall 2 which terminates in a peripherally disposed edge wall 4 having a constant radius of curvature and terminating in a peripheral flashing 6 oriented substantially parallel to the planar outer wall 2. Thus, the peripheral flashing 6 is spaced from the planar outer wall 2 by the radius defining the radiused edge wall 4 and defining the recess therein.

FIG. 2 further reflects an inlet tube 121 formed with a series of necked-down constrictions 123 along its length. This tube 121 can store samples of the contents of the bag 10 where each sample 125a, 125b, 125c, etc. can be sequestered from adjacent samples by sealing at the nearest constriction 123.

FIG. 5 shows the version where the second half is formed from a planar sheet 8 with the first half as described for FIGS. 2 through 4. In all embodiments, access is provided to an interior of the bag by way of at least one portal 12.

FIG. 2 and FIG. 3 each show three portals 12 allowing communication with the interior of the bag 10. The portal is formed concurrently with the first and second halves when the embodiment of FIGS. 2 through 4 are to be made. The portal 12 will appear on only one half of the bag in the FIG. 5 embodiment. FIG. 2 and FIG. 3 also reflect a sealed area 14 which defines an area of demarcation between a first compartment 16 and a second compartment 18 for the bag 10. Although illustrative, other compartments could be provided. The compartments 16 and 18 can be placed in fluid communication by means of a passageway 20 extending at both an upper and lower extremity of the sealed portion 14. Each passageway 20 can be subsequently heat sealed.

Typically, once the bag has been filled, the bag is massaged to urge the contents into both compartments 16 and 18. Further, the bag is manipulated to assure the segments in areas 125a, 125b, 125c, etc. are filled. Then a heat sealer can close passageways 20 (at 21) and at each constriction 123. This is desirable because once the bag is stored at cryogenic temperatures, it is preferred to minimize temperature spikes. Accordingly, a cutout 15 can appear along a central portion of sealed portion 14 so that a minimum amount of time is required to sever compartment 18 from 16. Conversely, no compartments are also contemplated as part of the invention. Please see the bag 10' of FIGS. 9 through 12 where like parts share like numerals.

FIG. 1 reflects a complementally formed female mold for allowing one half of the bag to be formed. As shown in FIG. 1, the female mold 30 includes a contour complemental to the bag so that the bag is a true reflection of the mold. More specifically, the planar outer wall 2 of bag 10 has its corresponding part in mold 30 as planar surface 32. Similarly, the radiused edge wall 4 of bag 10 finds its counterpart with radiused edge wall 34. Likewise, the peripheral flashing 6 finds its counterpart at the flashing support 36. In like manner, the access portals 12 are formed by portal recesses 42.

FIG. 6(A–C) shows first and second bag portion halves (6A, B, respectively) and assemblage (6C) of the two halves. Alternatively, FIGS. 6A and 6B could illustrate male mold halves over which planar blanks of plastic are draped and then deformed, for example, under heat and/or pressure. In such a case, the outer wall 2 of the bag portions are formed by mold wall 72. Radiused edge 4 is formed with edge 74. Access portals 12 are formed via projections 82. Partition 14 finds its counterpart in mold form 84 forming two compartments defined by 86 and 88.

Figure 13:
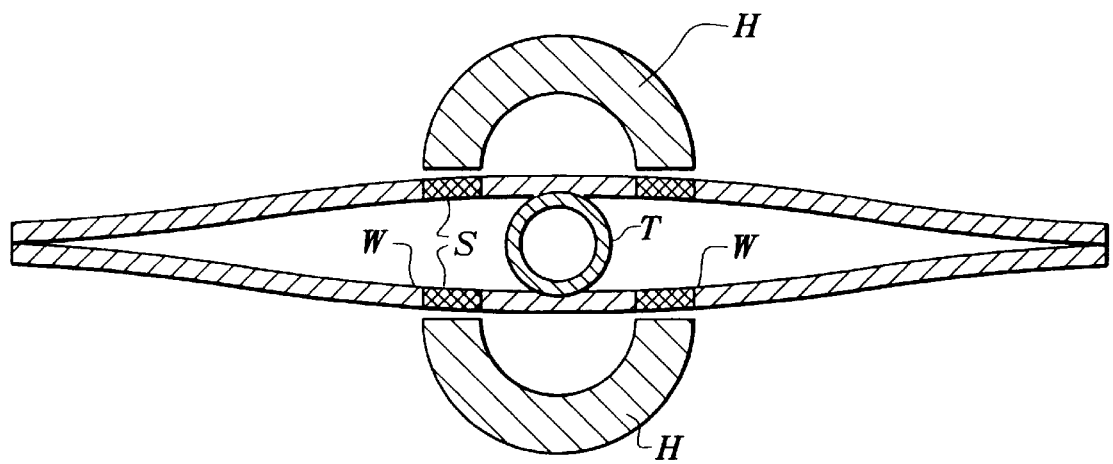
FIG. 13 reflects prior art technology in anchoring a port tube into a FIG. 8 type prior art bag.
Figure 14:
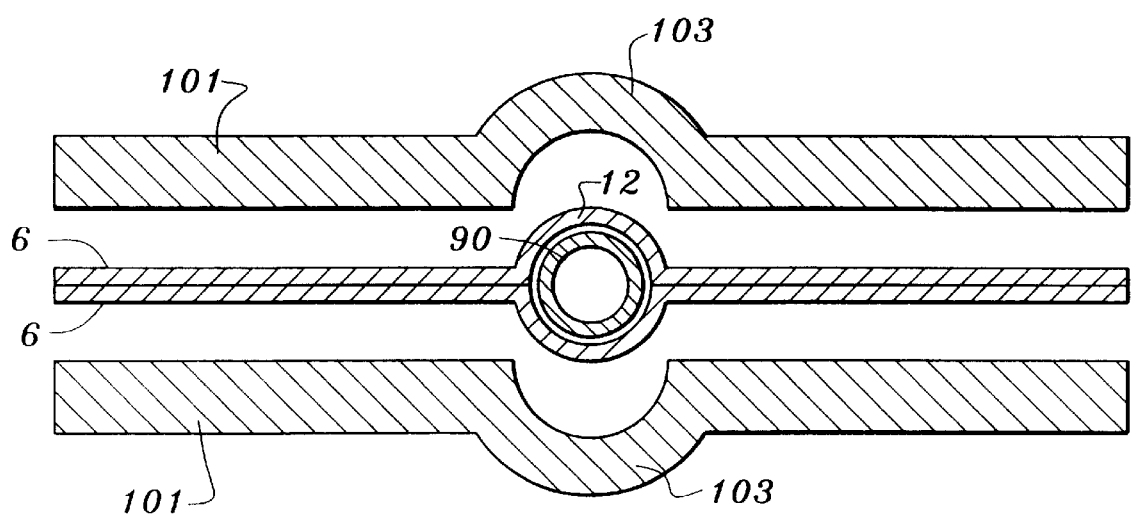
FIG. 14 reflects sealing structure and methodology for a port tube communicating through the bag according to one form of the present invention.

FIG. 14 reflects structure and methodology for placing a port tube 90 into a portal 12, as shown in FIG. 6C. One peripheral flange 6 is sealed to the other using a complemental RF die 101 which circumscribes the compartment(s) 16 (18, etc.). Where the die 101 contacts the portal 12, the die has a corresponding arcuate portion 103. Because the plastic which formed the portal was deformed as set forth in FIG. 1 (or 6), the plastic has uniform thickness throughout and particularly regarding the correct tubular shape. This results in a thicker and stronger sealing—joining area, especially as compared with FIG. 13. As the plastic is heated and cooled both during fabrication and use, it will have been stress relieved.

Figure 7:
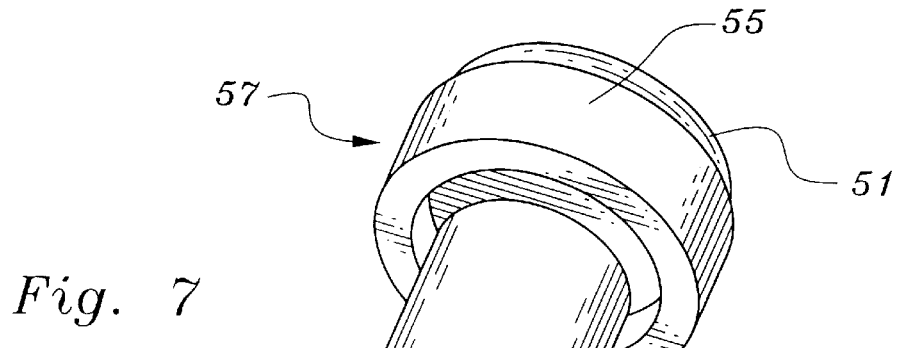
FIG. 7 is a perspective view of a mold plug.
Figure 8:
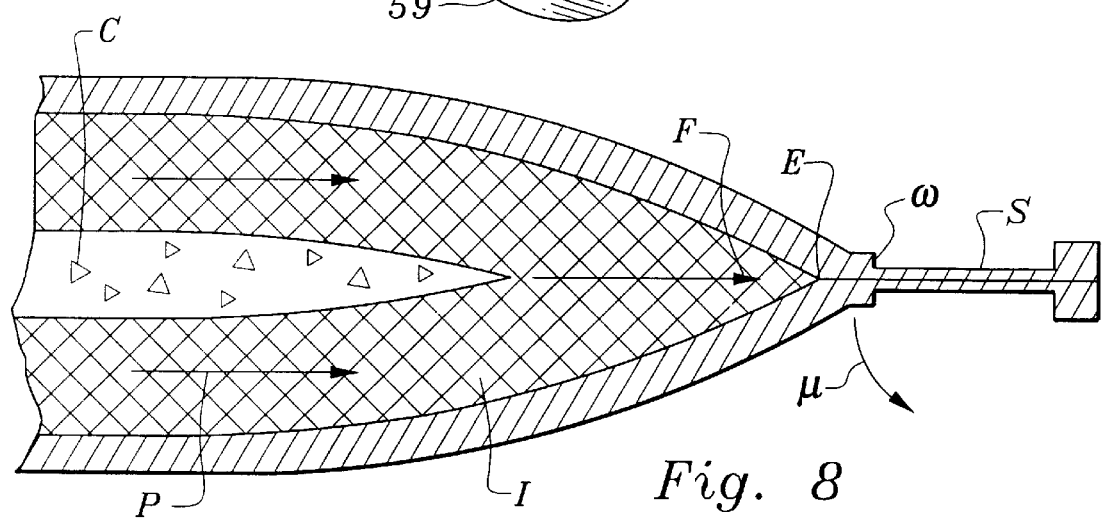
FIG. 8 reflects prior art bag structure and forces generated in prior art bags.

FIG. 7 shows a plug 57 to be received with the port tube 90 and with portal 12. The preform 57 comprises an inner first rod 53 and second concentric cylinder 55, connected by an annular top wall 51. Central to annular top wall 51 is a bore 59 extending partially into rod 53. The outer cylinder 55 is shorter than the inner rod 53.

The passageway 20 (FIG. 2) that allows communication between a first compartment and a second compartment 18 includes a relief area defining passageway 40 (FIG. 1) so that the first compartment forming recess 46 can communicate with the second compartment forming recess 48. A partition 49 constitutes the zone of demarcation between the adjacent compartments.

In fabrication, a sheet of plastic material overlies the mold 30 and the planar material is forced within the contour defined by the mold 30. This can be done by positive pressure on the side of the sheet of material opposite from the mold or it can be formed by vents V forming a vacuum within the mold cavity to draw the plastic down. The forming process can be coupled with heat and pressure and the plastics can be formed from a family of plastics characterized by their ability to deform and retain in memory their deformed state caused by the application of heat and or pressure.

Where the FIG. 5 bag is to be used, a substantially planar blank of plastic is placed in overlying registry with respect to the one preformed half defined by one planar outer wall, radiused edge wall and peripheral flashing and is adhered thereto by means of adhesive, ultrasonic welding or other fastening techniques.

Preferably, however, a second mold having mirror symmetry to the FIG. 1 mold (as in FIGS. 6A, B) allows a second half to be formed which is the mirror image of the first half. Thus, the peripheral flange defined by the peripheral flashing 6 is placed in overlying registry, aligning both halves (as shown in FIG. 6C) and then a welding technique can be used as mentioned above.

Figure 15:
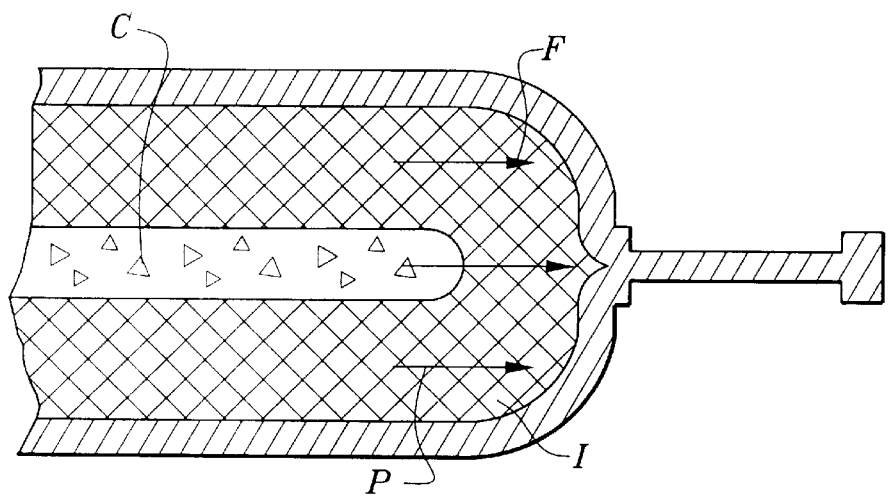
FIG. 15 depicts the improvement over FIG. 8.

The radiused edge wall includes the advantages illustrated in FIG. 15. First, the planar outer wall does not have any high spots and therefore presents a substantially uniform thickness along the entire length of the bag. In addition, the radiused edge wall minimizes the existence of stress areas by dissipating focusing forces so that failure of the bag at the seam site will have been made much less likely. Finally, the peripheral flashing provides an improved purchase area for causing two halves of the bag to be united since there is an abundance of material easily accessible for adherence either by an adhesive or by welding technology.

Having thus described the invention, it should be apparent that numerous structural modifications and adaptations may be resorted to without departing from the scope and fair meaning of the instant invention as set forth hereinabove and as described hereinbelow by the claims.

I claim:

1. A medical bag mold for forming medical bags which resist breakage especially when exposed to a phase change, comprising, in combination:

a recess defined by a planar surface, a radiused periphery circumscribing said planar surface in order to provide force dissipation of the bag at its periphery and a peripheral support circumscribing said radiused periphery and oriented parallel to said planar surface, and means for conforming a plastic sheet material blank to maintain a contour of the mold such that the conformed plastic sheet material results in a break resistant medical bag, having a complemental planar surface, radiused periphery and peripheral flashing circumscribing said radiused periphery.

2. The mold of claim 1 including a relief area projecting into a portion of said periphery support and a portion of said radiused periphery to define an access portal into a cavity of the mold for providing a portal into the formed medical bag.

3. The mold of claim 1 wherein said means for conforming said plastic sheet material blank to maintain a contour of the mold is pressure means operatively coupled to said mold.

4. The mold of claim 1 wherein said means for conforming said plastic sheet material blank to maintain a contour of the mold is heat means operatively coupled to said mold.

5. A mold for fixing fracture resistant medical bags into a fixed shape, comprising, in combination:

a substantially rectangular planar surface;

a peripheral support spaced from and parallel to and surrounding said planar surface; and a curved wall having a slope which changes along its entire extent when viewed in cross-section and extending from said planar surface to said peripheral support providing a constant radius ring transitioning between the surface and said support to provide medical bags which are fracture resistant and retain the shape fixed by the mold.

6. The mold of claim 5 including at least one partition extending perpendicularly from said planar surface and dividing the mold into at least two compartments.

7. A vacuum forming bag mold to form fixed shape medical bags which are resistant to fracture stress, comprising, in combination:
- a planar surface to receive a portion of a sheet material blank;
- a peripheral support to also receive another portion of the sheet material blank thereon and said support spaced from and parallel to said planar surface and connected by a wall which also receives a further portion of the sheet material blank;
- at least one relief area defining an access fluid receiving portal projecting from said wall and also receiving another portion of the sheet material blank; and
- said mold including means for causing the sheet material blank to be recontoured and held into a molded position.

8. The bag mold of claim 7 wherein said wall has a slope which changes along its entire extent when viewed in cross-section extending from said planar surface to said peripheral support.

9. The bag mold of claim 8 including at least one partition extending perpendicularly from said planar surface and dividing the mold into at least two compartments.

10. The bag mold of claim 9 including an access passageway between each said compartment and passing through each said partition.

11. The bag mold of claim 10 wherein said access passageway includes two channels per partition, one remote from the other.

12. The bag mold of claim 11 wherein the compartments are not of equal size.

13. The bag mold of claim 12 wherein a larger compartment includes at least two relief areas defining access portals.

14. The bag mold of claim 13 wherein a smaller compartment includes at least one relief area defining an access portal.

15. The bag mold of claim 14 further comprising means for conforming said sheet material blank to a contour of the mold and retain the contour.

16. The bag mold of claim 15 wherein said sheet material is comprised of a plastic material.

17. The mold of claim 16 including a sheet material forming cutout on the partition to provide a corresponding cutout on the sheet material.

18. A medical bag mold for forming medical bags comprising, in combination:
- a mold cavity defined by a recess including a planar surface, a radiused periphery circumscribing said planar surface and a peripheral support circumscribing said radiused periphery and oriented parallel to said planar surface,
- means for permanently conforming a sheet material blank to a contour of the mold, and
- a relief area to define an access portal into the mold cavity for providing a corresponding portal into the formed medical bag.

19. The mold of claim 18 including a partition projecting up from said planar surface and interposed within a portion of the mold dividing the mold into at least two compartments.

20. The mold of claim 19 including an access passageway between the first and second compartments and passing through the partition.

21. The mold of claim 20 including a portal located addressing each of the compartments.

22. The mold of claim 21 including a second mold having a mirror symmetry with the first mold and means for conforming said plastic sheet to a contour of the mold so that the bag formed thereby has a thickness twice the radius of one mold.

23. The mold of claim 21 including a second mold having a planar wall so that the bag formed thereby has one planar side.

24. The mold of claim 22 wherein said means for conforming the sheet material blank to a contour of the mold includes at least one vent on the mold for vacuum forming said blank of sheet material within the mold.

25. The mold of claim 24 wherein the second of said two compartments is larger than the first said compartment.

26. The mold of claim 25 further comprising a plurality of portals located addressing said larger compartment.

27. The mold of claim 26 wherein said portals formed are substantially cylindrical bores.

28. The mold of claim 27 wherein the mold is rigid.

29. The mold of claim 22 wherein said means for conforming the sheet material blank to a contour of the mold includes positive pressure means on the side of the sheet material opposite the mold.

30. The mold of claim 29 further comprising a heating means to aid in contouring the blank to the mold.

31. The mold of claim 28 wherein said relief area is located along one edge of said radiused periphery.

32. The mold of claim 31 wherein said plurality of portals comprises three portals within said second larger compartment and one portal in said first compartment.

33. The mold of claim 32 wherein at least one said portal is configured as an inlet tube having a series of constrictions along its length within which the liquid is contained, said constrictions allowing sealing thereat so that a series of liquid samples are formed between constrictions for individual removal.

34. A mold for forming medical bags comprising, in combination:
- a recess including a planar surface, a radiused periphery circumscribing said planar surface and a peripheral support circumscribing said radiused periphery and oriented parallel to said planar surface,
- means for conforming a sheet material blank to a contour of the mold such that the blank retains the mold contour,
- a relief area to define an access portal into the mold cavity for providing a portal into the formed bag,
- a partition interposed within a portion of the mold dividing the mold into at least two compartments,
- an access passageway between the first and second compartments and passing through said partition; and
- a portal located addressing each of said compartments.

35. A mold for forming medical bags which hold fluids used in a medical environment comprising, in combination:
- a recess including a planar surface, a radiused periphery circumscribing said planar surface and a peripheral support circumscribing said radiused periphery and oriented parallel to said planar surface,
- means for conforming a sheet material blank to a contour of the mold such that the blank subsequently retains the contour of the mold,
- a relief area to define an access portal into the mold cavity for providing a portal into the formed bag,
- a partition interposed within a portion of the mold dividing the mold into at least two compartments, an access passageway between the first and second compartments and passing through said partition, a portal located addressing each of said compartments, a second mold having a mirror symmetry with the first mold so that the medical bag formed thereby has a thickness twice the radius of one mold, wherein said means for conforming the sheet material blank to a contour of the mold includes at least one vent on the mold for vacuum forming said blank of sheet material within the mold, wherein the second of said two compartments is larger than the first said compartment, and further comprising a plurality of portals located addressing said larger compartment.

36. A mold for forming medical bags comprising, in combination:

a recess including a planar surface, a radiused periphery circumscribing said planar surface and a peripheral support circumscribing said radiused periphery and oriented parallel to said planar surface, and means for conforming a sheet material blank to a contour of the mold such that the blank subsequently retains the contour of the mold, including a relief area to define an access portal into the mold cavity for providing a portal into the formed bag, a partition interposed within a portion of the mold dividing the mold into at least two compartments, an access passageway between the first and second compartments and passing through said partition, a portal located addressing each of said compartments, a second mold having a mirror symmetry with the first mold so that the medical bag formed thereby has a thickness twice the radius of one mold, wherein said means for conforming the sheet material blank to a contour of the mold includes at least one vent on the mold for vacuum forming said blank of sheet material within the mold, wherein the second of said two compartments is larger than the first said compartment, further comprising a plurality of portals located addressing said larger compartment, wherein said portals formed are substantially cylindrical bores, wherein the mold is rigid, wherein said relief area is located along one edge of said radiused periphery, and wherein said plurality of portals comprises three portals within said second larger compartment and one portal in said first compartment.

37. A mold for forming medical bags, comprising, in combination:

a planar surface;

a peripheral support spaced from said planar surface;

a curved wall having a slope which changes along its entire extent when viewed in cross section extending from said planar surface to said peripheral support;

at least one partition extending perpendicularly from said planar surface and dividing the mold into at least two compartments;

an access passageway between each said compartment and passing through each said partition;

wherein said access passageway includes two channels, one remote from the other; and at least one relief area defining an access portal in at least one compartment of the mold.

38. A mold for forming medical bags, comprising, in combination:

a planar surface;

a peripheral support spaced from said planar surface;

a curved wall having a slope which changes along its entire extent when viewed in cross section extending from said planar surface to said peripheral support;

at least one partition extending perpendicularly from said planar surface and dividing the mold into two compartments;

an access passageway between each said compartment and passing through each said partition;

wherein said access passageway includes two channels, one remote from the other;

at least one relief area defining an access portal in at least one compartment of the mold;

wherein one of said two compartments is larger than the other said compartment; and wherein the larger said compartment includes at least two relief areas defining access portals.

39. The mold of claim 38 wherein said smaller compartment includes at least one relief area defining an access portal.

40. A mold for forming medical bags comprising, in combination:

a recess including a planar surface, a radiused periphery circumscribing said planar surface and a peripheral support circumscribing said radiused periphery and oriented parallel to said planar surface, means for conforming a sheet material blank to a contour of the mold such that the blank subsequently conforms to the contour of the mold, a partition interposed within a portion of the mold dividing the mold into at least two compartments, and a portal located addressing each of said compartments.

41. A mold for forming medical bags comprising, in combination:

a recess including a planar surface, a radiused periphery circumscribing said planar surface and a peripheral support circumscribing said radiused periphery and oriented parallel to said planar surface, means for conforming a sheet material blank to a contour of the mold such that the blank subsequently conforms to the contour of the mold, a relief area to define an access portal into the mold cavity for providing a portal into the formed bag, a partition interposed within a portion of the mold dividing the mold into at least two compartments, an access passageway between the first and second compartments and passing through said partition, a portal located addressing each of said compartments, a second mold having a mirror symmetry with the first mold so that the medical bag formed thereby has a thickness twice the radius of one mold, wherein said means for conforming the sheet material blank to a contour of the mold includes at least one vent on the mold for vacuum forming said blank of sheet material within the mold, wherein the second of said two compartments is larger than the first said compartment, further comprising a plurality of portals located addressing said larger compartment, and wherein said plurality of portals comprises three portals within said second larger compartment and one portal in said first compartment.

42. A mold for forming medical bags, comprising, in combination:

a planar surface;

a peripheral support spaced from said planar surface;

a curved wall having a slope which changes along its entire extent when viewed in cross section extending from said planar surface to said peripheral support;

at least one partition extending perpendicularly from said planar surface and dividing the mold into at least two compartments; and including at least one relief area defining an access portal in at least one compartment of the mold.

43. The mold of claim 42 wherein one of said two compartments is larger than the other said compartment, and wherein the larger said compartment includes at least two relief areas defining access portals.

44. A mold for forming medical bags, comprising, in combination:

a planar surface;

a peripheral support spaced from said planar surface; and a curved wall having a slope which changes along its entire extent when viewed in cross section extending from said planar surface to said peripheral support, at least one partition extending perpendicularly from said planar surface and dividing the mold into two compartments, an access passageway between each said compartment and passing through each said partition, wherein said access passageway includes two channels, one remote from the other, at least one relief area defining an access portal in at least one compartment of the mold, wherein one of said two compartments is larger than the other said compartment, and wherein said smaller compartment includes at least one relief area defining an access portal.

45. A mold for forming fracture resistant medical bags which retain the shape of the mold, comprising, in combination:

a substantially rectangular planar surface;

a peripheral support spaced from and parallel to and surrounding said planar surface;

a curved wall having a slope which changes along its entire extent when viewed in cross section extending from said planar surface to said peripheral support providing a constant radius ring transitioning between the surface and said support; and including at least one partition extending perpendicularly from said planar surface and dividing the mold into at least two compartments.

46. The mold of claim 45 including an access passageway between each said compartment and passing through each said partition.

47. The mold of claim 46 wherein said access passageway includes two channels, one remote from the other.

48. The mold of claim 47 including at least one relief area defining an access portal in at least one compartment of the mold.

49. The mold of claim 48 wherein the mold includes two compartments.

50. The mold of claim 49 wherein one of said two compartments is larger than the other said compartment.

51. The mold of claim 50 wherein the larger said compartment includes at least two relief areas defining access portals.

52. The mold of claim 51 wherein said smaller compartment includes at least one relief area defining an access portal.

53. The mold of claim 52 further comprising means for conforming a plastic sheet material blank to a contour of the mold.

54. The mold of claim 48 further comprising a second mold complemental to said first mold and a mirror image thereof for forming a complete bag.

55. The mold of claim 54 including a portal located addressing each of the compartments.

56. A vacuum forming medical bag mold, comprising, in combination:

a planar surface;

a peripheral support to receive a sheet material blank thereon and said support spaced from and parallel to said planar surface connected by a wall;

at least one relief area defining an access fluid receiving portal projecting from said wall;

wherein said wall has a slope which changes along its entire extent when viewed in cross-section extending from said planar surface to said peripheral support; and including at least one partition extending perpendicularly from said planar surface and dividing the mold into at least two compartments.

* * * * *